United States Patent
Bifano et al.

(10) Patent No.: US 10,018,817 B2
(45) Date of Patent: Jul. 10, 2018

(54) ADAPTIVE OPTICS FOR IMAGING THROUGH HIGHLY SCATTERING MEDIA IN OIL RESERVOIR APPLICATIONS

(71) Applicants: Aramco Services Company, Houston, TX (US); SAUDI ARABIAN OIL COMPANY, Dhahran (SA); TRUSTEES OF BOSTON UNIVERSITY, Boston, MA (US)

(72) Inventors: Thomas Bifano, Mansfield, MA (US); Shannon L. Eichmann, Somerville, MA (US); Bennett B. Goldberg, Newton, MA (US); Mazen Kanj, Dhahran (SA); Hari P. Paudel, Boston, MA (US); William Shain, Brookline, MA (US)

(73) Assignees: ARAMCO SERVICES COMPANY, Houston, TX (US); SAUDI ARABIAN OIL COMPANY (SA); TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 15/061,056

(22) Filed: Mar. 4, 2016

(65) Prior Publication Data
US 2016/0259156 A1 Sep. 8, 2016

Related U.S. Application Data

(60) Provisional application No. 62/128,302, filed on Mar. 4, 2015.

(51) Int. Cl.
*G01J 1/58* (2006.01)
*G02B 21/00* (2006.01)
(Continued)

(52) U.S. Cl.
CPC ..... *G02B 21/0028* (2013.01); *G01N 21/6458* (2013.01); *G02B 21/002* (2013.01);
(Continued)

(58) Field of Classification Search
CPC ... G01N 2201/0696; G01N 2201/0697; G01N 2201/0675; G02B 21/0032; G02B 21/33;
(Continued)

(56) References Cited

U.S. PATENT DOCUMENTS

| 4,628,468 A | 12/1986 | Thompson et al. |
| 5,034,613 A | 7/1991 | Denk et al. |

(Continued)

OTHER PUBLICATIONS

J.T. Fredrich, "3D Imaging of Porous Media using Laser Scanning Confocal Microscopy with Application to Microscale Transport Processes"; Geomechanics Department 6117, Sandia National Laboratories, Albuquerque, NM 87185-0751, USA; Phys. Chem. Earth (A), vol. 24, No. 7; pp. 551-561; 1999.
(Continued)

*Primary Examiner* — Taeho Jo
(74) *Attorney, Agent, or Firm* — Bracewell LLP; Constance Gall Rhebergen

(57) ABSTRACT

Embodiments of the invention provide an imaging system and method using adaptive optics and optimization algorithms for imaging through highly scattering media in oil reservoir applications and lab-based petroleum research. Two-/multi-photon fluorescence microscopy is used in conjunction with adaptive optics for enhanced imaging and detection capabilities in scattering reservoir media. Advanced fluorescence techniques are used to allow for super-penetration imaging to compensate for aberrations both in and out of the field of interest, extending the depth at which pore geometry can be imaged within a rock matrix beyond the current capability of confocal microscopy. The placement of a Deformable Mirror or Spatial Light Modu-
(Continued)

lator for this application, in which scattering and index mismatch are dominant aberrations, is in an optical plane that is conjugate to the pupil plane of the objective lens in the imaging system.

14 Claims, 5 Drawing Sheets

(51) Int. Cl.
  *G02B 21/02* (2006.01)
  *G01N 21/64* (2006.01)
  *G02B 27/00* (2006.01)
  *G02B 21/36* (2006.01)

(52) U.S. Cl.
  CPC ....... *G02B 21/008* (2013.01); *G02B 21/0032* (2013.01); *G02B 21/0048* (2013.01); *G02B 21/0076* (2013.01); *G02B 21/02* (2013.01); *G02B 27/0068* (2013.01); *G01N 2201/0675* (2013.01); *G02B 21/367* (2013.01)

(58) Field of Classification Search
  CPC .............. G02B 21/002; G02B 27/0025; G02B 21/0028; G02B 27/0012; G02B 21/008; G02B 2207/114; G02B 26/103; G02B 21/0048
  USPC ...................................................... 250/458.1
  See application file for complete search history.

(56) References Cited

U.S. PATENT DOCUMENTS

| | | | |
|---|---|---|---|
| 6,128,077 A * | 10/2000 | Jovin | G01J 3/10 356/310 |
| 7,668,586 B2 | 2/2010 | Hyman et al. | |
| 8,107,156 B2 | 1/2012 | George et al. | |
| 8,300,669 B2 | 10/2012 | Dantus et al. | |
| 8,629,413 B2 | 1/2014 | Betzig et al. | |
| 8,771,978 B2 | 7/2014 | Ragan | |
| 8,866,107 B2 | 10/2014 | Cui | |
| 8,908,925 B2 | 12/2014 | Hurley et al. | |
| 2006/0033933 A1* | 2/2006 | Feierabend | G01J 9/00 356/512 |
| 2006/0071143 A1* | 4/2006 | Saggau | G02B 21/002 250/201.3 |
| 2007/0068341 A1* | 3/2007 | Cheng | B22F 1/0096 75/255 |
| 2008/0316571 A1* | 12/2008 | MacAulay | G02B 21/06 359/239 |
| 2009/0027769 A1* | 1/2009 | Saito | G02B 9/60 359/385 |
| 2009/0137990 A1* | 5/2009 | Sheinis | A61F 9/008 606/5 |
| 2009/0185191 A1* | 7/2009 | Boppart | A61B 5/0066 356/479 |
| 2010/0245766 A1* | 9/2010 | Zhang | A61B 5/0059 351/206 |
| 2010/0245770 A1* | 9/2010 | Zhang | A61B 5/0059 351/219 |
| 2010/0296533 A1* | 11/2010 | Silverstein | G02B 27/48 372/29.02 |
| 2011/0004447 A1 | 1/2011 | Hurley et al. | |
| 2011/0004448 A1 | 1/2011 | Hurley et al. | |
| 2011/0134436 A1* | 6/2011 | Podoleanu | A61B 3/1015 356/512 |
| 2011/0170180 A1* | 7/2011 | Turner | G02B 26/0825 359/385 |
| 2012/0070817 A1 | 3/2012 | Wang et al. | |
| 2013/0057953 A1* | 3/2013 | Yokoi | G02B 21/002 359/388 |
| 2013/0181143 A1* | 7/2013 | Betzig | G02B 21/0032 250/459.1 |
| 2013/0182253 A1* | 7/2013 | Cui | G01N 21/49 356/338 |
| 2014/0009808 A1* | 1/2014 | Wang | G02F 1/33 359/10 |
| 2014/0055852 A1* | 2/2014 | Vizi | G02B 21/06 359/385 |
| 2014/0104618 A1 | 4/2014 | Potsaid et al. | |
| 2015/0015879 A1 | 1/2015 | Papadopoulos et al. | |
| 2015/0153554 A1* | 6/2015 | Tamano | G02B 21/002 359/380 |
| 2016/0169801 A1* | 6/2016 | Rogacs | G01N 15/1429 506/9 |
| 2016/0327779 A1* | 11/2016 | Hillman | G02B 21/367 |

OTHER PUBLICATIONS

Hari P. Paudel et al., "Axial range of conjugate adaptive optics in two-photon microscopy"; Optical Society of America; 2015; 8 pages.
Nicholas G. Horton et al., "In Vivo Three-Photon Microscopy of Subcortical Structures within an Intact Mouse Brain"; Nature Photonics; Mar. 2013; 14 pages.
Jianyong Tang et al. "Superpenetration optical microscopy by iterative multiphoton adaptive compensation technique"; PNAS vol. 109, No. 22; May 29, 2012; 10 pages.
Y. Lu et al., "Spherical aberration correction in aplanatic solid immersion lens imaging using a MEMS deformable mirror"; Microelectronics Reliability 52, 2012; pp. 2120-2122.
Martin J. Booth, "Adaptive optical microscopy: the ongoing quest for a perfect image"; Light: Science & Applications (2014) 3, e165, doi. 10.1038/lsa.2014.46, published Apr. 25, 2014; 7 pages.
Jerome Mertz et al., "Field of view advantage of conjugate adaptive optics in microscopy applications"; Jan. 11, 2015; 11 pages.
Benard, et al: "Three-Dimensional Imaging of Sulfides in Silicate Rocks at Submicron Resolution with Multiphoton Microscopy." Microscopy and Microanalysis, vol. 17, No. 6, Dec. 1, 2011, pp. 937-943.
Bifano, et al: "Beam Control in Multiphoton Microscopy Using a MEMS Spatial Light Modulator." Optomechatronic Mico/Nano Devices and Components III: Oct. 8-10, 2007, Lausanne, Switzerland [Proceedings of SPIE, ISSN 0277-786X].
Kus, et al: "Application of Confocal Laser-Scanning Microscopy (CLSM) to Autofluorescent Organic and Mineral Matter in Peat, Coals and Siliciclastic Sedimentary Rocks—A Qualitative Approach," International Journal of Coal Geology, vol. 137, pp. 1-18, Oct. 27, 2014.
International Search Report and Written Opinion for related International application PCT/US2016/021004 dated Sep. 1, 2016.

* cited by examiner

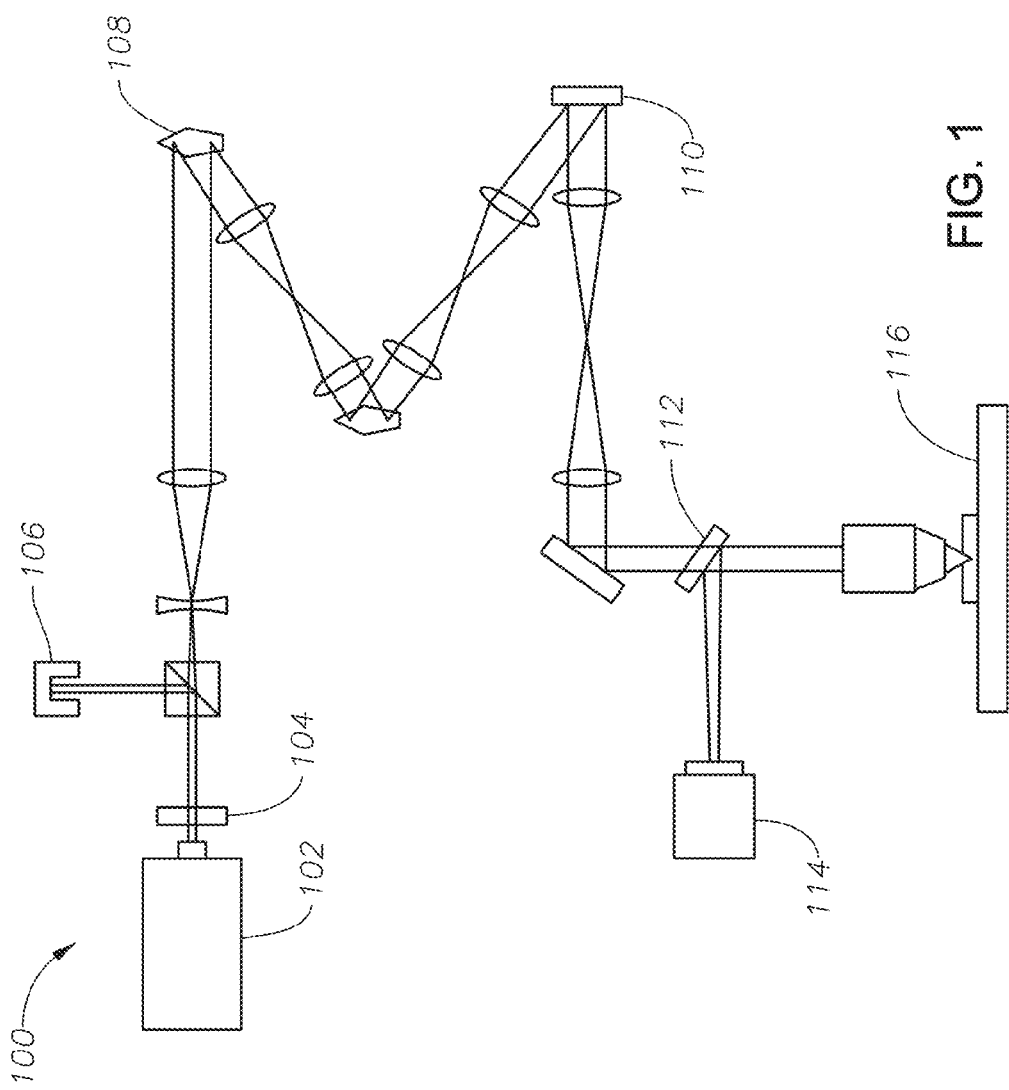
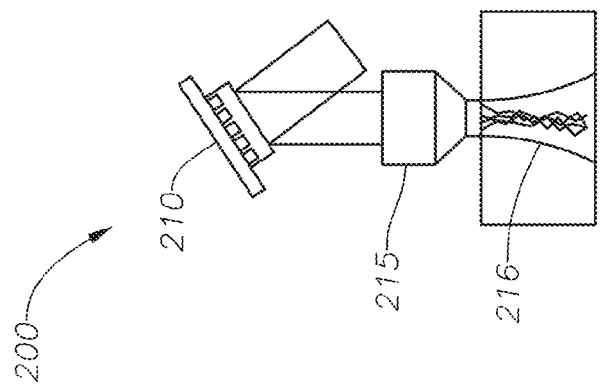
FIG. 1
FIG. 2

ADAPTIVE OPTICS FOR IMAGING THROUGH HIGHLY SCATTERING MEDIA IN OIL RESERVOIR APPLICATIONS

CROSS REFERENCE TO RELATED APPLICATION

This application claims the benefit of and priority under 35 U.S.C. § 119 to Provisional Patent Application 62/128,302 entitled Adaptive Multi-Photon Imaging of Subsurface Nanoparticle Flow in Porous Rock filed Mar. 4, 2015.

BACKGROUND

Field of the Invention:

The present invention generally relates to an imaging system for two-dimensional (2D) and three-dimensional (3D) imaging through highly scattering media in oil reservoir applications. In particular, this imaging system uses adaptive optics along with two/multi-photon microscopy in order to enhance an image quality through scattering media, observe additives (i.e. tracers, nanoparticles, and fluids) contained within reservoir rock or other scattering media, and to detect features and characteristics of reservoir rock and fluids.

Description of the Related Art:

Exploratory imaging of regions for oil and gas reserves is important in order to properly identify and extract hydrocarbons from the ground. A petroleum or oil and gas reservoir is a subsurface pool of hydrocarbons contained in porous rock formations. Rock formations trap the naturally occurring hydrocarbons and exploration methods are used to remove these hydrocarbons for further processing. Visualizing oil/water interfaces, nanoparticles, and nanoparticle mobility within reservoir rock at the sub-micron scale is a critical step toward understanding fluid and nanoparticle transport and developing appropriate models of this mobility at the reservoir scale. The objects of interest are inherently embedded below the rock surface and within the optically scattering pore structure. Many microscopy techniques have been used to image subsurface particles before, but there is a long standing problem in optical microscopy where when imaging objects of interest through scattering media, the objects of interest routinely embedded within scattering media or behind thick surfaces become blurred when they are imaged because the scattering of light obscures and distorts the image. Visualizing oil/water interfaces, nanoparticles, and nanoparticle mobility within and not simply at the surface of reservoir rock on the sub-micron scale is a critical step toward understanding fluid and nanoparticle transport and developing appropriate models of this mobility in the reservoir scale. When this transport is understood more fully it can be used to study how best to deliver materials and recover them in order to extract hydrocarbons efficiently.

Imaging fluid flow deep inside rock samples provides the most accurate representation of porous media properties. However, scattering results from imaging below the surface of the rock because of index mismatch between the solid rock phase and the fluid-filled pores. The medium is thus optically heterogeneous leading to a large amount of light scattering. The depth at which the scattering background fully obscures the image is called the transport-mean-free path (L*).

For example, in water-filled limestone, L* is on the order of 50-60 um. Therefore traditional techniques are limited to imaging the surface or near-surface flow of the liquid. However, this invention overcomes the limited ability to image the near-surface flow of liquid through Super-penetration Multi-Photon Microscopy (SP-MPM), which uses a spatial light modulator (SLM) to optimize the phase of the coherent light focused on the sample, compensating for scattering and thereby enhancing the two-photon signal. This optimization can be done at any depth, allowing for imaging deep within the sample.

Another problem associated with fluorescent microscopy is that many sub-micron fluorescent particles embedded either in an oil/water mixture or within rock pores yield few photons and are therefore difficult to image and characterize. New sophisticated techniques in two/multi-photon microscopy have recently been developed for semiconductor and biological imaging and provide the capability to image deeper within highly scattering media. One example of two-photon fluorescence microscopy (2 PM) provides imaging of sub-cortical structures at a spectral excitation window of 1,700 nm in a mouse-brain. The goal in such applications is to create an imaging method to counteract wave-front distortions caused by aberration and random scattering. However this imaging method is limited in its field of view and is good for smaller imaging applications.

The terms two-photon and multi-photon refer to the absorption of two or more photons of infrared light that are used to excite fluorescence as opposed to the use of single photon absorption in the visible wavelength range, where the use of infrared light provides a means to reduce scattering. Until now, however, these new techniques have not been applied to porous reservoir rock, oil/water interfaces, nanoparticles, tracers contained in produced fluids or in reservoir rock pieces. Furthermore, these techniques do not include adaptive optics to correct for image aberrations due to scattering interfaces either away from or in the field-of-view (FOV).

Traditionally, Computed Tomography (CT) and Nuclear Magnetic Resonance (NMR) techniques are used to characterize and image reservoir rock at the millimeter scale or at the micrometer scale with micro-CT both with and without fluids. Typically, however, when seeking information about dynamic systems (i.e. fluids, tracers, surfactants, nanoparticles, polymers, etc.) in real reservoir rock these techniques do not offer the necessary spatial or temporal resolution required. Other techniques such as optical microscopy (i.e. epifluorescence, laser scanning confocal microscopy, and total internal reflection microscopy) offer better spatial and temporal resolution but these techniques are greatly affected by noise due specifically to optical scattering thus they are mostly limited to use with transparent, solid and smooth surfaces. Additionally, of these optical techniques, only confocal microscopy is able to image in 3D.

In general, confocal microscopy uses laser light and a polished thin section of rock chip that is vacuum-pressure impregnated with fluorescing epoxy. Scans of the rock chip measure reflected or fluorescent light intensity in regularly spaced planes. 3D pore geometries are analyzed after the images are stacked using 3D visualization software. Many devices employ a multipoint statistical model in order to image the subsurface region and employ measured reflection data and noise reduction algorithms to identify noise data in the retrieved set of images, thereby creating a 3D model of the pore structure.

Laser scanning confocal microscopy (LSCM) is widely used in the biomedical community and has proved useful for imaging the pore space of reservoir rocks by filling the pores of thin sections with cured fluorescently tagged epoxy. Confocal microscopy systems are commercially available through most microscope vendors and take a series of 2D fluorescent images at multiple depths that are reconstructed into a 3D rendering of pore volume. For reservoir rocks, the pores of thin sections (<50 microns) and thick section (<250 microns) are filled with fluorescently tagged epoxy under vacuum and then cured to lock the bright fluorescent tags within the pore space. For thin sections (<50 microns) the epoxy can be imaged with the rock matrix intact but for thicker sections (<250 microns) the rock matrix must be removed through chemical methods and the epoxy cast is then imaged alone. While this technique is typically used with mobile fluids in the biomedical community, these fluids are transparent which would not be the case for crude oil samples and imaging within reservoir rock.

Traditional optical microscopy techniques fail to image deep into strongly scattered reservoir rock in the presence of oil-water mixtures. These techniques also fail to explore the dynamic motion of nanoparticles, tracers and fluid-fluid interfaces, due largely to the strong optical scattering of the light encountered at all interfaces of differing optical index, including, but not limited to variations in the material, variations in the fluids, variations in the pore walls and debris within any fluids. In addition, LSCM, which can image up to 50 microns within a rock matrix, requires that the pores be filled and cured with fluorescently tagged epoxy which renders the segment of rock useless for fluid flow purposes.

A well-known strategy to counteract aberrations makes use of adaptive optics (AO), as borrowed from astronomical imaging. Adaptive optics consists of inserting an element in the imaging optics, such as a deformable mirror (DM), which imparts inverse aberrations to the imaged light, compensating for the aberrations induced by the sample or the microscope system itself. While the optical problem of astronomy is similar to microscopy, the details of the system are different: astronomical imaging typically involves sparse, stationary signals through a dynamic medium such as turbulent atmosphere, as opposed to imaging multiple moving beads through the static rock pores.

Placement of the SLM is very important in this kind of microscopy because it can lead to further benefits in media characterization. Some inventions include that the continuous mirror or SLM is placed near the objective and not explicitly conjugated to the aperture. One drawback for placing the optical element out of the pupil plane for out-of-pupil conjugation is that even though it produces larger fields of view, this design reduces the number of actuators across the beam. The actuators act to produce a shape that corrects for the wave-front distortions. If only a few actuators are used, the shape is limited and cannot be corrected properly.

More actuators allow for better distortion correction. Another way to combat the distortion problem is to place the wave-front converting element conjugate to the pupil in order to correct the aberrations. The wave-front converting element can be used to correct for aberrations. Specifically a wave-front converting element in a laser scanning microscope (LSM) is not placed in a plane conjugate with the pupil in order to improve off-axis performance, so that loss of light can be minimized and the apparatus can be simplified. Some inventions include that the continuous mirror or Spatial Light Modulator (SLM) is placed near the objective and not explicitly conjugated to the aperture.

Specifically, adaptive optics in the form of a Kilo-DM wave-front corrector from Boston Micro-machines is also currently being used in the industry, which can be programmed to provide for specific optical corrections. The adaptive optics reconstruct a complete diffraction limited wide-field wave front in order to correct the image aberrations. Also, combining high and low resolution data using laser scanning fluorescence microscopy (LSFM) provides further advantages in imaging subsurface material. By combining high resolution LSFM scans with CT scans, larger volumes of rocks are captured to create a fuller picture of the porous material.

Some imaging devices provide for excitation in a target material by absorbing two photons. Fluorophores are excited by a conventional laser operating at twice the single-photon excitation wavelength. For power efficiency, a pulsed laser is used instead of a continuous wave laser. A dichroic mirror filters the fluorescence onto a photomultiplier tube or alternative fluorescent detector, and scanning mirrors sweep the focal spot across the sample (beam-scanning). Some implementations keep the focal spot stationary and instead use motorized stages to sweep the sample through the focal spot (sample-scanning). The fluorescence at each transverse position is recorded and processed to form the image. The main benefit of adaptive optics is the correction of aberrations that derive from the heterogeneous refractive index structure of the rock that is being imaged. The refractions from optical index variations lead to aberrations that affect the resolution and contrast of the image. These aberrations vary among different rock structures and so correcting them in real time is important for different rock formations. Furthermore, imaging at different depths tends to provide more scattering and aberrations and the techniques described herein go to enhancing these images to track and image fluid, tracer, and nanoparticle flow.

There is a need to develop systems and methods for using two/multi-photon fluorescence microscopy in conjunction with adaptive optics including deformable mirrors for enhanced imaging and detection capabilities in reservoir media. There is also a need to use advanced fluorescence techniques to allow for super-penetration imaging in conjunction with adaptive optics to compensate for aberrations both in and out of the field of interest beyond the current technologies in the field of confocal microscopy. The invention enables imaging of dynamic and stationary nanoparticles, surfactants, fluid-fluid interfaces and tracers which can be used to study properties such as diffusion, mobility, adhesion, stickiness, and wettability within the 3D pore structure of cores and thin sections. Furthermore, larger volumes of fluid will be sampled thus improving the detection of tracers and nano-particles at the well-site.

SUMMARY

Accordingly, embodiments of the invention have been made to provide a Super-Penetration Multi-Photon Microscope (SP-MPM) using a pupil-conjugate Spatial Light Modulator (SLM) to modify the phase of the coherent light focused into the sample. After an initial scan of the rock sample from the laser, the system calculates the optimum wave-front phase map using an optimization algorithm. The optimum wave-front phase map is then applied to the signal returned to the SLM to create an optimum image.

According to at least one embodiment of the invention, there is provided a SP-MPM system which images static and mobile beads on the far side of 30-um rock sections. A single layer of nanometer to micron sized fluorescent beads is deposited on a glass slide and imaged using an 880 nm laser at 1 frame-per-second (fps). The fluorescent light is filtered by a dichroic mirror onto a Thorlabs PMT-TIA60. Two galvanometric mirrors are used for scanning. A segmented deformable mirror such as a 1020 segmented BMC kilo SLM, is used to adjust the phase in the pupil plane.

According to at least one embodiment, there is provided a Coherent Ti-Sapphire laser that is focused onto the sample using a 0.8NA W, 20 mm WD 3 mm Nikon Objective.

According to at least one embodiment, the two-photon spread function (PSF) can be about 300 nm. Beads behind 30 um of rock appear blurry, and are 1-2% of the unobscured intensity. The SLM is used to enhance the signal at the center of the image, increasing the diminished signal by a factor of 10.

According to at least one embodiment, the optimal enhancement algorithm is determined by a recursion algorithm, that cycles through using two-dimensional, orthogonal modes and their corresponding amplitude coefficients. The invention also includes the use of adaptive optics and optimization algorithms to correct for aberrations both within the porous structure of reservoir rock and at the surface interfaces as well as within turbid fluids. Furthermore, the invention includes using focusing techniques to image at multiple depths within a rock sample with and without aplanatic solid immersion lenses. The adaptive optics and deformable mirrors can detect tracers and nanoparticles through ticker layers/larger volumes of produced fluids by using longer wavelengths and aberration corrections. The invention provides the ability to image 3D pore structure of reservoir rock such as cores and thick/thin sections, using cured fluorescent epoxy and dynamic fluorescent entities such as nanoparticles, reservoir tracers, and dye molecules at depths greater than 50 microns. Also interfacial properties, like surface interactions, aggregation, adhesion, and wettability of the dynamic nanoparticles, tracers, fluorophores, and fluid-fluid interfaces within rocks and in produced fluids at the well site or in the laboratory can be imaged.

According to at least one embodiment, the penetration of light into the produced fluids and sampled volume of produced fluids can be increased for better detection of fluid type, nanoparticle flow in the fluids, and tracers. Also, the deformable mirrors and optimization algorithms can be used to correct for aberrations at varying depths of produced fluids. Image stitching can then be used at multiple positions to increase the size of the area of correction with the deformable mirror and optimization algorithms and also increases the field of view within the reservoir rock.

According to at least one embodiment, a Hadamard basis was chosen to offset the scattering induced by the rock which is of high frequency. The advantage of this is that each basis pattern strongly perturbs the input signal, allowing for a clear indication of the appropriate amplitude for that pattern. Moreover, the rectangular symmetry of the Hadamard patterns match the symmetry of the segmented DM, allowing for precise linear implementation.

According to at least one embodiment, the invention provides a laser scanning multi-photon fluorescence microscope system for imaging dynamic and stationary particles, fluorescent molecules, and fluid interfaces in reservoir scattering media. The system comprises a two/multi-photon laser for generating a laser beam; a deformable mirror in an optical plane, which is conjugate to the pupil plane of an objective lens, with a segmented light modulator or a continuous mirror surface, for modifying a phase of coherent light of the laser beam focused on a sample; two pairs of conjugate lenses with two galvanometric scanners in an optical or pupil conjugate plane with the deformable mirror; a microscope objective with a back pupil where the deformable mirror can image the beam in order to focus the beam and collect a fluorescence signal; and an image processing device with a digitizer for digitizing the fluorescence signal, processing the collected fluorescence values and displaying the results with a stitched image.

According to at least one embodiment, the fluid flow is tracked using an algorithm that allows imaging of individual particles.

According to at least one embodiment, the fluid flow is tracked using smaller image windows and faster scan rates than the stationary images.

According to at least one embodiment, the effective field of view for a given pattern is extended over the image plane.

According to at least one embodiment, the image is optimized at the center allowing for recovery of intensity in a region around the center of the image.

According to at least one embodiment, the deformable mirror uses the auto-fluorescence from the scattering media as an optimization source.

According to at least one embodiment, the optimization pattern is taken for each location and then stitched together with patterns from other locations to increase the field of view.

According to at least one embodiment, the scattering media consists of porous media, rock pieces, rock thin sections, turbid fluids, oil-water mixtures, mineralogical samples, and rock mimics.

According to at least one embodiment, there is provided a laser scanning multi-photon fluorescence microscope method for imaging dynamic and stationary particles, fluorescent molecules, and fluid interfaces in reservoir scattering media. The method includes the steps of pulsing a laser to create a two/multi-photon laser beam; expanding the beam with two pairs of conjugate lenses in an optical conjugate plane with two galvanometric mirrors; filling a deformable mirror aperture with the beam; modifying the phase of the coherent light of the laser beam focused on the sample with a deformable mirror that is in an optical plane conjugate to the pupil plane of an objective lens; focusing the beam and collecting a fluorescence signal from the sample with a microscope objective; digitizing the fluorescence signal; processing the collected fluorescence values; and displaying the results with a stitched image with an image processor and a display device.

According to at least one embodiment, the method further includes the step of tracking the fluid flow using an algorithm that allows imaging of individual particles.

According to at least one embodiment, the method further includes the step of tracking fluid flow using smaller image windows and faster scan rates than the stationary images.

According to at least one embodiment, the method further includes the step of extending the effective field of view for a given pattern over the image plane.

According to at least one embodiment, the method further includes the step of optimizing the image at the center allowing for recovery of intensity in a region around the center of the image.

According to at least one embodiment, the method further includes the step of using the auto-fluorescence from the scattering media as an optimization source.

According to at least one embodiment, the method further includes the step of applying the optimization pattern to each location and then stitching together the optimization patterns from other locations to increase the field of view.

Another embodiment includes that the scattering media consists of porous media, rock pieces, rock thin sections, turbid fluids, oil-water mixtures, mineralogical samples, and rock mimics.

Various objects, advantages and features of the invention will become apparent from the following description of embodiments with reference to the accompanying drawings.

BRIEF DESCRIPTION OF DRAWINGS

These and other features, aspects, and advantages of the invention are better understood with regard to the following Detailed Description, appended Claims, and accompanying Figures. It is to be noted, however, that the Figures illustrate only various embodiments of the invention and are therefore not to be considered limiting of the invention's scope as it may include other effective embodiments as well.

FIG. 1 is a schematic of the Super-Penetration Multi-Photon Microscope System (SP-MPM).

FIG. 2 is a schematic showing a wave-front control of light to allow tight focus within scattering media.

DETAILED DESCRIPTION

Figure 3:
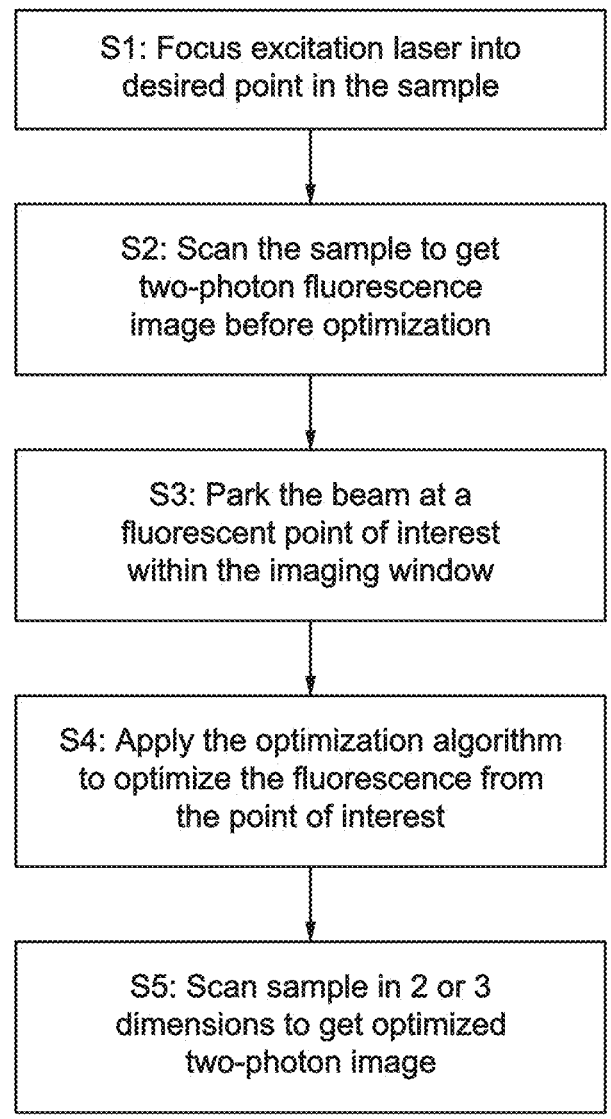
FIG. 3 is a flow-chart view of the method whereby the subsurface material is imaged.

Advantages and features of the present invention and methods of accomplishing the same will be apparent by referring to embodiments described below in detail in connection with the accompanying drawings. However, the present invention is not limited to the embodiments disclosed below and may be implemented in various different forms. The embodiments are provided only for completing the disclosure of the present invention and for fully representing the scope of the present invention to those skilled in the art.

For simplicity and clarity of illustration, the drawing figures illustrate the general manner of construction, and descriptions and details of well-known features and techniques may be omitted to avoid unnecessarily obscuring the discussion of the described embodiments of the invention. Additionally, elements in the drawing figures are not necessarily drawn to scale. For example, the dimensions of some of the elements in the figures may be exaggerated relative to other elements to help improve understanding of embodiments of the present invention. Like reference numerals refer to like elements throughout the specification.

Hereinafter, various embodiments of the present invention will be described in detail with reference to the accompanying drawings.

Embodiments of the invention relate to a microscope system, which uses two-/multi-photon fluorescence microscopy in conjunction with adaptive optics for enhanced imaging and detection in reservoir media. The invention uses two photon and multi-photon light sources for super-penetration with adaptive optics in the form of deformable mirrors in order to compensate for aberrations both in and out of the field of interest. The invention extends the depth of detection and imaging beyond the current technologies used in the oil field and increases the depth at which pore geometry and velocity of liquids within the pores can be imaged within the rock matrix using cured epoxy.

The invention implements a closed-loop optimization algorithm using a deformable mirror in order to maximize the multi-photon signal from a single point, thereby compensating for aberrations both in and out of the field of interest. As this optimization can be performed independent of the thickness and scattering properties of the sample, the invention extends the depth of detection and imaging beyond the current technologies used in the oil field and increases the depth at which pore geometry and velocity of liquids within the pores can be imaged within the rock matrix using cured epoxy. Traditional confocal microscopy uses ultraviolet and visible wavelength light sources, which scatter more than near infrared light sources. The adaptive optics allow correction due to scattering and create a non-blurry image unlike the imaging techniques using ultraviolet and visible wavelength light sources.

FIG. 1 shows the microscope system 100. The microscope system 100 in FIG. 1 consists of two main sets of components: the imaging system and the optimization algorithm. Components of the imaging system include a laser excitation source 102. The laser excitation source 102 can be various lasers and one embodiment includes a 2.9 watt, 140 fs, 80 MHZ repetition rate Ti-sapphire laser (coherent Chameleon) operated at 880 nm. Other suitable lasers could be used depending on the type of image and depth required. The laser power is controlled by a motorized half wave plate 104, which in this embodiment is a Thorlabs AHWP05M-980 and also a polarization beam splitter 106, which is a Thorlabs GT5-B. Other half wave plates and beam splitters can be used as well.

In FIG. 1, a laser from a wavelength tunable, pulsed laser 102 is passed through a mirror controlled by a polarizer 104 and a polarization beam splitter 106. The laser beam is then expanded to fill the DM aperture 110. Two pairs of conjugate lenses 108 are used to place two galvanometric scanners in an optical conjugate plane (or pupil conjugate plane) with the DM 110. The DM 110 is then imaged onto the back pupil of a microscope objective 112 which is used for beam focusing and fluorescence collection. The fluorescence signal is detected using a photomultiplier tube 114. The amplified signal is then digitized using a digitizer on a PC card.

When optimizing the beam, the focused illumination beam is perturbed sequentially using orthogonal Hadamard modes by the DM 110. To implement optimization, the coefficient of each of the Hadamard bases is adjusted sequentially to maximize the optimization metric which is the two-photon/multi-photon emission intensity. The coefficient in terms of waves of each Hadamard basis is calculated using three-step phase shifting interferometry. For each Hadamard mode, every spatial segment of the SLM will be assigned either a 1 or a 0 according to the definition of that Hadamard mode. The segments assigned 0's are not perturbed at all, while the segments that are assigned is are perturbed at least three times in their optical path distance (i.e. phase) by an amount equal to a known fraction of the incident wavelength. The intensity at each point of interest in the image plane is measured for each perturbation. Over the full $2*\pi$ range of perturbation, that intensity is expected to vary in a sinusoidal manner as a function of the perturbation phase.

If $I_1$, $I_2$, and $I_3$ are the metrics at 0, $\pi$ and $\pi/2$, then the coefficient for a particular Hadamard basis is given by $$\tan^{-1}\left(\frac{I_1 - I_3}{2I_2 - I_1 - I_3}\right).$$

Further, the process is repeated for all 1024 Hadamard bases, and the optimum Hadamard patterns are added together to give the optimal-correction phase map, which is then applied to the beam in order to image the material. Thus, with three points of measurement, a sinusoidal fit can be made and the phase corresponding to maximum intensity can be estimated. This phase value becomes the coefficient for the Hadamard mode being evaluated.

Furthermore, the invention implements a procedure to stitch optimized patterns together to increase the field-of-view (FOV). This allows for larger regions to be imaged deeper within the scattering media. Once the optimization patterns are put together to form an overall pattern the microscope enables the user to collect images at video rates thus providing a pathway toward imaging individual mobile nanoparticles and interfaces.

In certain embodiments, the two pairs of doublet achromatic lenses 108 can have f1=145 mm and f2=245 mm and are conjugate to two orthogonally scanning galvanometric mirrors (Thorlabs GVS011) to the pupil DM 110, which can be a Boston Micromachines Corp. Kilo-DM 2. This DM can include 1020 segmented actuators, with a 10 kHz update rate, 1.5 um stroke, and conjugated itself to the back aperture or pupil of the microscope objective. A Nikon N16XLWd-PF 16× with an NA of 0.8 and a WD of 3 mm can also be used.

When the microscope operates, the two-photon fluorescence produced by the sample 116 is collected in an epifluorescence mode and routed with a dichroic mirror 108, collection lens 112 and emission filter to a photomultiplier tube 114, whereupon the photo-current is amplified by a trans-impedance preamplifier and digitized by a 14-bit digitizer. The digitizer is operated in an external trigger mode for fast data transfer synchronized to the update clock of the DM driver or to a frame clock generated by a DAC card.

In tests, a phase screen was used to introduce aberrations in the imaging, and to counteract the aberrations image-based iterative feedback optimization is used, where the fluorescence intensity serves as the optimization metric. The excitation focus was placed at the center of the sample for pupil AO correction and used a sequential optimization technique with 1024 Walsh orthogonal modes. For conjugate AO the whole beam was scanned over the entire image FOV and optimized the total fluorescence intensity per image based on a stochastic parallel gradient descent algorithm. The speed of the optimization is increased by acquiring sparse representations of these images using a much faster Lissajou scan pattern.

A further example of subsurface imaging with the present system includes using an aplanatic solid immersion lens (aSIL) microscopy method with a deformable mirror (DM) to image substrate depth. The method is used where the DM is conjugated to the back pupil plane of the objective.

FIG. 2 shows a microscope system 200, which uses wave-front control of refractions to allow tight focus within scattering media contained in the sample 216. In general the segmented light modulator (SLM) 210 is a laser scanning apparatus, where the laser beam can be directed through the objective 215 and onto the sample 216 to image the lower portions of the rock. The illumination beam can go off the side as shown in the figure.

According to at least one embodiment, there is a laser scanning multi-photon microscope called the Super-Penetration Multi-Photon Microscopy microscope as shown in FIG. 2. This microscope is capable of high-order aberration correction to image features at high resolution deeper than is possible with conventional fluorescence microscopes or laser scanning confocal microscopes. This incorporates multi-photon fluorescence microscopy with adaptive optics to image deep within highly scattering media and can also be combined with aplanatic solid immersion lenses to further increase resolution.

The imaging system is a two-photon (or multi-photon) fluorescence microscope that has been modified to include a microelectromechanical systems (MEMS) deformable mirror (DM) used to correct for the effects of scattering and aberrations in the sample by modifying the wave-front of the scanning beam as shown in FIG. 2.

The optimization algorithm is used to determine the optimum wave-front phase map, which is then applied to the imaging system. The imaging system uses a segmented light modulator described below to implement the algorithm and to further image the subsurface regions of the rock.

Segmented light modulators (SLM) refers to a deformable mirror and specifically in this embodiment a Kilo-SLM can be used.

FIG. 3 shows a method that the apparatus employs. In step S1, the sample is positioned using a 3-axis motorized stage such that the desired measurement volume is near the focal spot. In step S2, the sample is then scanned with the scanning mirror, with the resulting fluorescence filtered by a dichroic mirror onto a photomultiplier tube, generating a voltage proportional to the intensity at each scan point. The voltages are discretized by an analog-to-digital converter and processed with an image-processing program to form an initial image. In step S3, the laser is focused onto a desired point of optimization, chosen based on the initial image and the desired imaging volume. The power is adjusted to maximize the signal-to-noise ratio of the desired optimization point. In step S4, the recursion optimization algorithm is run on the DM, thereby optimizing the signal at that spot. In step S5, the sample is re-scanned with the DM now applying the optimal phase pattern, generating an optimized image. The sample can be translated axially and re-scanned to generate a stack of images with an optimized volume centered around the initial optimized point.

Figure 4:
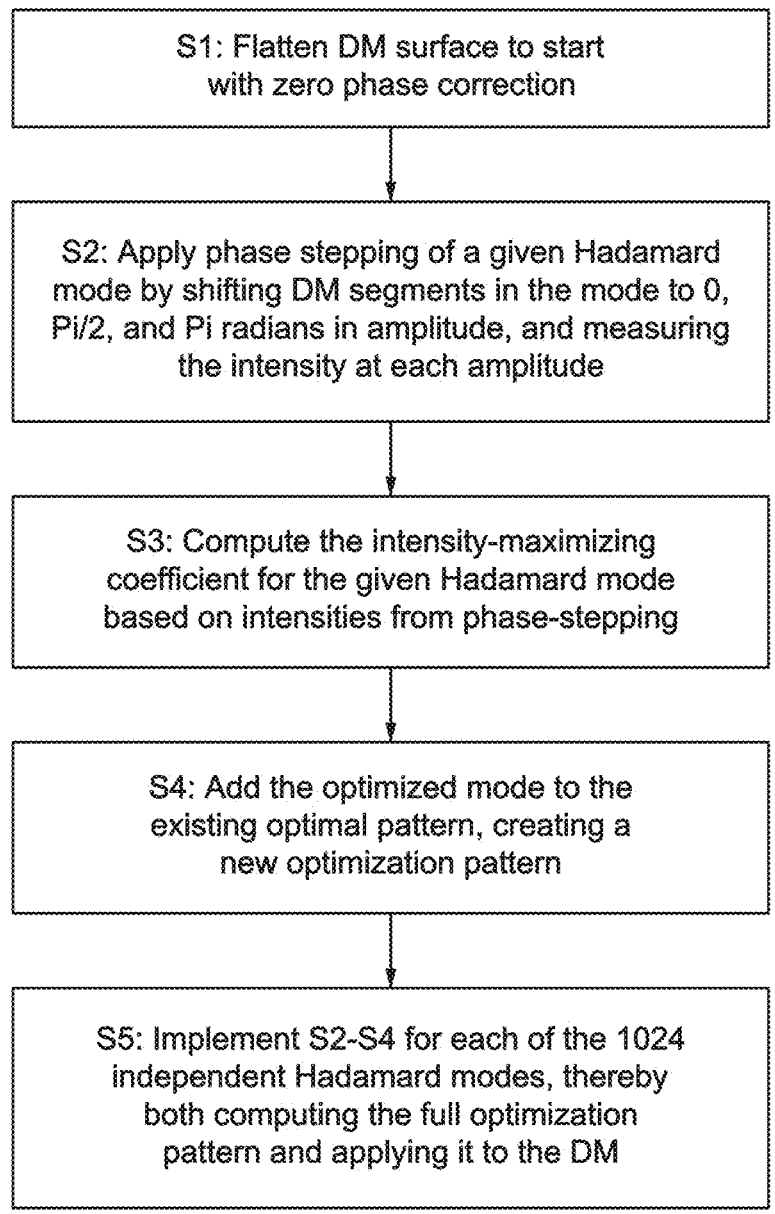
FIG. 4 is a flow-chart view of generating the optimization algorithm.

FIG. 4 is a flow chart for running the recursion optimization algorithm to generate the enhancement pattern. In step S1, a flat (zero-phase) pattern is applied to the DM. In step S2, phase-stepping is implemented by applying a given Hadamard mode to the mirror with amplitudes of 0, $\pi$, and $\pi/2$ and recording the optimization metric (two-photon fluorescence) for each amplitude. In step S3, the optimal coefficient of a given basis mode is determined: if $I_1$, $I_2$, and $I_3$ are the metrics at 0, $\pi$ and $\pi/2$, then the optimal coefficient for this Hadamard basis mode is given by $$\tan^{-1}\left(\frac{I_1 - I_3}{2I_2 - I_1 - I_3}\right).$$

In step S4, the mode optimized in steps 2 and 3 is multiplied by the optimal coefficient and summed with the pre-existing optimization pattern to create a new, more accurate optimal phase pattern, which is applied to the DM. In step S5, steps 2 through 4 are then repeated for each of the 1024 basis modes, with the result that the Hadamard patterns are added together sequentially with intensity-maximizing coefficients to give the optimal-correction phase map.

Figure 5:
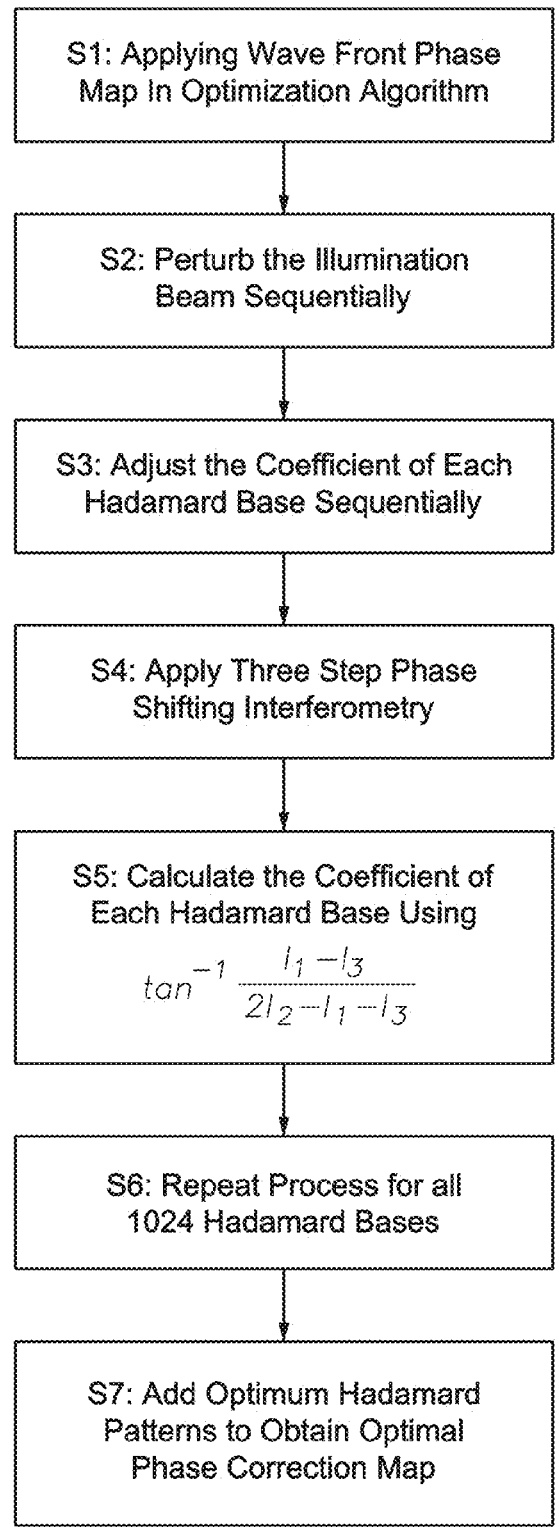
FIG. 5 is flow chart of applying the wave front phase map in the optimization algorithm.

FIG. 5 is a flow chart for running the recursion optimization algorithm to generate the enhancement pattern. Step S1 is the first step, that is the process begins for applying the wave front phase map in the optimization algorithm. Next in step S2, the focused optimization beam is perturbed sequentially using orthogonal Hadamard modes. To determine the proper perturbation to counteract the scattering, a coefficient for each Hadamard basis is determined S3 and they are placed into the algorithm using three-step phase shifting interferometry S4. The coefficient of each base is adjusted to maximize the optimization metric or the two-photon/multi-photon emission intensity. Step S5, then calculates each base by determining the result of the equation that if $I_1$, $I_2$, and $I_3$ are the metrics at 0, $\pi$ and $\pi/2$, then the coefficient for this Hadamard basis is given by $$\tan^{-1}\left(\frac{I_1 - I_3}{2I_2 - I_1 - I_3}\right).$$

Further the process is repeated for all 1024 Hadamard bases in Step S6, and then the optimum Hadamard patterns are added together to give the optimal-correction phase map in step S7.

Figure 6:
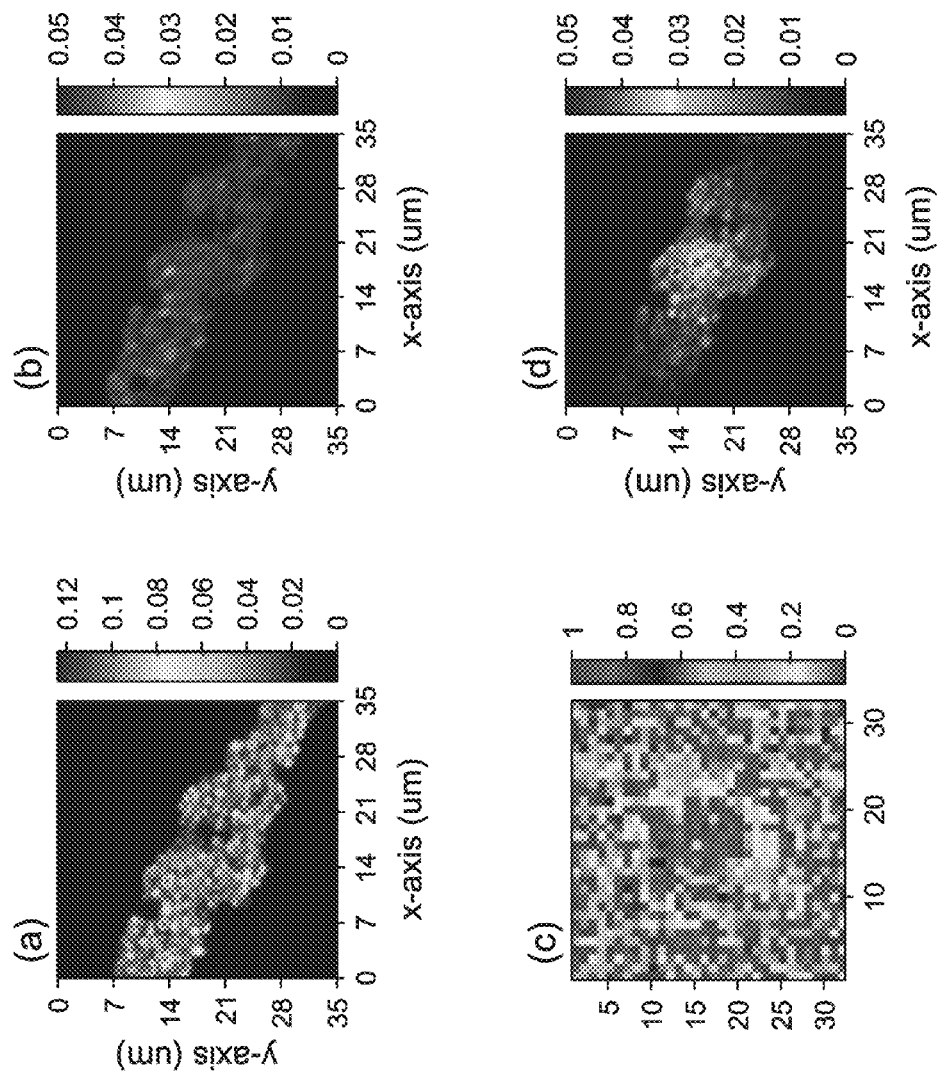
FIG. 6 is a representative set of images showing a 10um ×10um image with 1 um diameter beads through a rock section (around 100 microns thick). The FOV increases by 10× by optimizing at multiple points.

FIG. 6 is an example of 10 um×10 um images of 1 um diameter beads through a rock section around 100 microns thick. After optimizing an initial point, we chose multiples nearby maxima to optimize as well. The resulting FOV increases 10× by optimizing at multiple points. The first image (a) shows before optimization, the second (b) is a single optimization, the third (c) is a local maxima highlighted and the fourth (d) is a stitched image.

What is claimed is:

1. A laser scanning multi-photon fluorescence microscope system for imaging dynamic and stationary particles, fluorescent molecules, and fluid interfaces in reservoir scattering media, the system comprising:
   a two/multi-photon laser for generating a laser beam;
   a deformable mirror in an optical plane, which is conjugate to the pupil plane of an objective lens, with a segmented light modulator or a continuous mirror surface, for modifying a phase of coherent light of the laser beam focused on a sample;
   two pairs of conjugate lenses with two galvanometric scanners in an optical conjugate plane with the deformable mirror;
   a microscope objective with a back pupil where the deformable mirror can image the beam in order to focus the beam and collect a fluorescence signal;
   an image processing device with a digitizer for digitizing the fluorescence signal, processing the collected fluorescence values and displaying the results with a stitched image; and
   wherein a fluid flow is tracked using smaller image windows and faster scan rates than with stationary images.

2. The laser scanning system of claim 1, wherein the fluid flow is tracked using an algorithm that allows imaging of individual particles.

3. The laser scanning system of claim 1, wherein an effective field of view for a given pattern is extended over an image plane.

4. The laser scanning system of claim 1, wherein an image is optimized at the center allowing for recovery of intensity in a region around the center of the image.

5. The laser scanning system of claim 1, wherein the deformable mirror uses an auto-fluorescence from a scattering media as an optimization source.

6. The laser scanning system of claim 5, wherein the scattering media consists of porous media, rock pieces, rock thin sections, turbid fluids, oil-water mixtures, mineralogical samples, and rock mimics.

7. The laser scanning system of claim 1, wherein an optimization pattern is taken for each location and then stitched together with patterns from other locations to increase a field of view.

8. A laser scanning multi-photon fluorescence microscope method for imaging dynamic and stationary particles, fluorescent molecules, and fluid interfaces in reservoir scattering media, the method comprising the steps of:
   pulsing a laser to create a two/multi-photon laser beam;
   expanding the beam with two pairs of conjugate lenses in an optical conjugate plane with two galvanometric mirrors;
   filling a deformable mirror aperture with the beam;
   modifying the phase of the coherent light of the laser beam focused on the sample with a deformable mirror that is in an optical plane conjugate to the pupil plane of an objective lens;
   focusing the beam and collecting a fluorescence signal from the sample with a microscope objective;
   digitizing the fluorescence signal;
   processing the collected fluorescence values;
   displaying the results with a stitched image with an image processor and a display device; and
   tracking fluid flow is tracked using smaller image windows and faster scan rates than with stationary images.

9. The laser scanning method of claim 8, further including a step of tracking the fluid flow using an algorithm that allows imaging of individual particles.

10. The laser scanning method of claim 8, further including a step of extending an effective field of view for a given pattern over the image plane.

11. The laser scanning method of claim 8 further including a step of optimizing the image at the center allowing for recovery of intensity in a region around the center of the image.

12. The laser scanning method of claim 8, further including a step of using an auto-fluorescence from the scattering media as an optimization source.

13. The laser scanning method of claim 12, further including that the scattering media consists of porous media, rock pieces, rock thin sections, turbid fluids, oil-water mixtures, mineralogical samples, and rock mimics.

14. The laser scanning method of claim 8, further including a step of applying the optimization pattern to each location and then stitching together the optimization patterns from other locations to increase a field of view.

* * * * *